(12) United States Patent
Lantela et al.

(10) Patent No.: US 11,406,679 B2
(45) Date of Patent: Aug. 9, 2022

(54) TERPENE ENRICHMENT METHODS AND SYSTEMS

(71) Applicant: Whister Technologies Corp., Vancouver (CA)

(72) Inventors: Daniel Erik Lantela, Whistler (CA); Brishna Soraya Kamal, Whistler (CA); Kelvin Kin-Wing Wong, Whistler (CA)

(73) Assignee: WHISTLER TECHNOLOGIES CORP., Vancouver (CA)

( * ) Notice: Subject to any disclaimer, the term of this patent is extended or adjusted under 35 U.S.C. 154(b) by 0 days.

(21) Appl. No.: 16/759,645

(22) PCT Filed: Oct. 30, 2018

(86) PCT No.: PCT/CA2018/051374
§ 371 (c)(1),
(2) Date: Apr. 27, 2020

(87) PCT Pub. No.: WO2019/084679
PCT Pub. Date: May 9, 2019

(65) Prior Publication Data
US 2020/0281995 A1    Sep. 10, 2020

Related U.S. Application Data

(60) Provisional application No. 62/578,971, filed on Oct. 30, 2017.

(51) Int. Cl.
*A61K 36/00* (2006.01)
*A61K 36/185* (2006.01)
*A61K 9/00* (2006.01)

(52) U.S. Cl.
CPC .......... *A61K 36/185* (2013.01); *A61K 9/0056* (2013.01); *A61K 2236/37* (2013.01)

(58) Field of Classification Search
None
See application file for complete search history.

(56) References Cited

U.S. PATENT DOCUMENTS

| 9,259,449 B2 | 2/2016 | Raderman |
| 2016/0279073 A1 | 9/2016 | Donsky et al. |
| 2016/0346339 A1 | 12/2016 | Finley et al. |
| 2017/0008870 A1 | 1/2017 | Dibble et al. |
| 2017/0022132 A1 | 1/2017 | Mona, III et al. |
| 2017/0280740 A1 | 10/2017 | Goldstein et al. |
| 2018/0143212 A1 | 5/2018 | Giese et al. |

FOREIGN PATENT DOCUMENTS

| CN | 1691954 A | 11/2005 |
| CN | 102281932 A | 12/2011 |
| CN | 102413681 A | 4/2012 |
| CN | 103182268 | 7/2013 |
| CN | 205740906 U | 11/2016 |
| CN | 106458338 A | 2/2017 |
| CN | 106488970 A | 3/2017 |
| EA | 200300485 A1 | 10/2003 |
| EP | 1536810 B1 | 8/2012 |
| WO | 2004/016277 A2 | 2/2004 |
| WO | 2016/064987 A1 | 4/2016 |
| WO | 2017/051398 A1 | 3/2017 |
| WO | 2018/000094 A1 | 1/2018 |
| WO | 2019/056126 A1 | 3/2019 |
| WO | 2019/240581 A1 | 12/2019 |

OTHER PUBLICATIONS

Examination Report No. 1 issued in connection with Australian Patent Application No. 2018360729, IP Australia, dated Jul. 13, 2021.
Office Action and Search Report issued in connection with Chinese Patent Application No. 201880071290.5, CNIPA, dated Jul. 15, 2021.
Extended European Search Report and Search Opinion issued in connection with European Patent Application No. 18874011.2, European Patent Office, dated Jul. 26, 2021.
"Pressure Cooker Cannabis Butter—Instant Pot Decarb & Extraction," Jan. 29, 2018, pp. 1-20,https://www.reddit.com/r/instantpot/comments/7ohk9q/pressure_cooker_cannabis_butter/. Accessed Feb. 3, 2021.
"Decarb under pressure to retain terps?," Apr. 24, 2018, pp. 1-9, https://future4200.com/t/decarb-under-pressure-to-retainterps/551. Accessed Feb. 3, 2021.
Golwalkar K., 'Process Reactors' in: Process Equipment Procurement in the Chemical and Related Industries 2015, Nov. 26, 2014, pp. 63-75, https://doi.org/10.1007/978-3-319-12078-2_6.
Patent Examination Report 1 dated Jan. 17, 2022 issued on corresponding New Zealand Patent Application No. 764977, pp. 1-6.
Notification regarding defects in patent application dated Jan. 23, 2022 issued on corresponding Israeli Patent Application No. 274140, pp. 1-5.

(Continued)

*Primary Examiner* — Michael V Meller
(74) *Attorney, Agent, or Firm* — Dentons Canada LLP (57) ABSTRACT

The present disclosure provides methods and systems producing active extraction products from cannabis resin. An example method comprises introducing a mixture of a resin and an extractor into a sealed container, heating the mixture to extract cannabinoids and terpenes from the resin, adding water to the mixture, cooking the mixture and water, for example at high temperature and pressure for a predetermined time period to decarboxylate the cannabinoids, allowing the mixture and water to cool and separate, and removing an active extraction product from an upper portion of the sealed container.

16 Claims, 5 Drawing Sheets

(56) References Cited

OTHER PUBLICATIONS

International Search Report and Written Opinion for PCT/CA2018/051374, International Searching Authority, dated Feb. 21, 2019.
International Preliminary Report on Patentability for PCT/CA2018/051374, International Preliminary Examining Authority, dated Nov. 27, 2019.
Search Report issued in connection with Chinese Patent Application No. 201880071290.5, China National Intellectual Property Administration, dated May 9, 2022.
Second Office Action issued in connection with Chinese Patent Application No. 201880071290.5, China National Intellectual Property Administration, dated May 13, 2022.

TERPENE ENRICHMENT METHODS AND SYSTEMS

CROSS REFERENCE TO RELATED APPLICATION

This application claims the benefit of priority of U.S. Provisional Patent Application No. 62/578,971 filed Oct. 30, 2017, which is hereby incorporated herein by reference in its entirety.

TECHNICAL FIELD

The present disclosure relates to extraction and decarboxylation of compounds from cannabis.

BACKGROUND

Cannabis contains many compounds of medicinal and commercial significance, including cannabinoids and terpenes. A large fraction (often>50%) of the terpenes are lost upon drying of the plant. Most extractions rely on dried material to make final products which results in a significant loss of terpenes before extractions. Furthermore, current solvent extraction processes, such as ethanol extraction, lose much of the terpenes during extraction. Finally, cannabis products which intend to use the therapeutic effects of cannabinoids must undergo a decarboxylation process, and optional winterization and work up steps, and this can cause further terpene losses.

The inventors have determined a need for improved methods and systems for extraction of compounds from cannabis.

SUMMARY

One aspect of the present disclosure provides a method of producing active extraction products from cannabis resin. The method comprises introducing a mixture of a resin and an extractor into a sealed container, heating the mixture to extract cannabinoids and terpenes from the resin; adding water to the mixture, cooking the mixture and water at temperature in a range of approximately 90-140 Celsius under a pressure in a range of approximately 0-420 kPa over atmospheric pressure for a period of about 1-25 hours to decarboxylate the cannabinoids, allowing the mixture and water to cool and separate for a period of about 8-24 hours, and removing an active extraction product from an upper portion of the sealed container.

The extraction product may comprise a cannabinoid to terpene ratio by mass in the range of about 1:1 to 20:1. Terpenes may comprise at least 5% of active compounds in the active extraction product. When made from fresh cannabis resin, the active extraction product can be enriched in terpenes by up to 150% as compared to the terpene content of dried cannabis of the same cultivar.

In some embodiments the method comprises filtering resin from the mixture after extracting cannabinoids and terpenes. In some embodiments filtering resin occurs prior to cooking the mixture.

In some embodiments the extractor comprises an edible lipid. In some embodiments the extractor comprises a hydrophobic organic solvent. In some embodiments the method comprises evaporating solvent and removing residues from the extraction product.

In some embodiments the method comprises removing a residual mixture from a bottom portion of the sealed container and separating water and extractor from the residual mixture to produce a secondary extraction product. In some embodiments the method comprises introducing the secondary extraction product into the sealed container with the mixture.

Further aspects of the invention and details of example embodiments are set forth below.

DRAWINGS

The following figures set forth embodiments in which like reference numerals denote like parts. Embodiments are illustrated by way of example and not by way of limitation in the accompanying figures.

DETAILED DESCRIPTION

The following disclosure provides methods and associated apparatus and systems for creating terpene rich cannabis extracts from cannabis resin in a single vessel reaction. In some embodiments, the starting material used is cannabis resin separated from fresh or frozen plant material. In some embodiments, the cannabinoids are decarboxylated while still in a mixture with the terpenes, resin and an extractor.

Certain embodiments provide methods and systems for producing decarboxylated extraction products (sometimes referred to as "orally active" extraction products, or simply "active" extraction products). As described in detail below, starting from fresh or frozen cannabis (plant matter or physically separated cannabis resin) an extract can be made which retains a higher proportion of terpenes to cannabinoids than are found in dried cannabis material or the extracts made thereof. Even starting from material that is dried, the extraction and decarboxylation process will retain more terpenes than typical cannabis extraction processes. Fresh cannabis is infused directly into a solvent or edible food matrix and decarboxylated, and final oil separated in a single pressurized extraction vessel. Oil is filtered and separated from any water remaining.

For simplicity and clarity of illustration, reference numerals may be repeated among the figures to indicate corresponding or analogous elements. Numerous details are set forth to provide an understanding of the examples described herein. The examples may be practiced without these details. In other instances, well-known methods, procedures, and components are not described in detail to avoid obscuring the examples described. The description is not to be considered as limited to the scope of the examples described herein.

In an example method according to the present disclosure, fresh cannabis resin, also known as bubble hash, is used as a starting material for an extraction process. As described below, the resin is mixed with an extractor comprising either a hydrophobic organic solvent or an edible lipid such as coconut oil. In example embodiments, the mixture of resin and extractor is heated, and then separated under particular conditions to produce a final active product which has a relatively high level of terpenes compared to products produced by other methods using the same starting material. In other words, certain embodiments provide extraction methods that result in less terpene loss than other methods typically employed in the art.

The extracts with the highest concentration of terpenes from a particular batch of cannabis will be produced from cannabis resin made from fresh cannabis material which is utilized for extraction directly after harvest (or which is frozen directly after harvest and utilized for extraction later). The cannabis resin may, for example, be obtained by processing plant material as described in International Patent Application No. PCT/CA2018/051197, which is hereby incorporated by reference herein.

After being made into bubble hash, or cannabis resin, the resin may be dissolved into solvent or oil immediately for processing by methods according to the present disclosure or may be frozen for future use. In some embodiments, the ratio (by mass) of resin to extractor is in the range of about 1:1.5 to 1:3 if the extractor is an edible oil, or about 1:2 to 1:10 if the extractor is a hydrophobic organic solvent.

Figure 1:
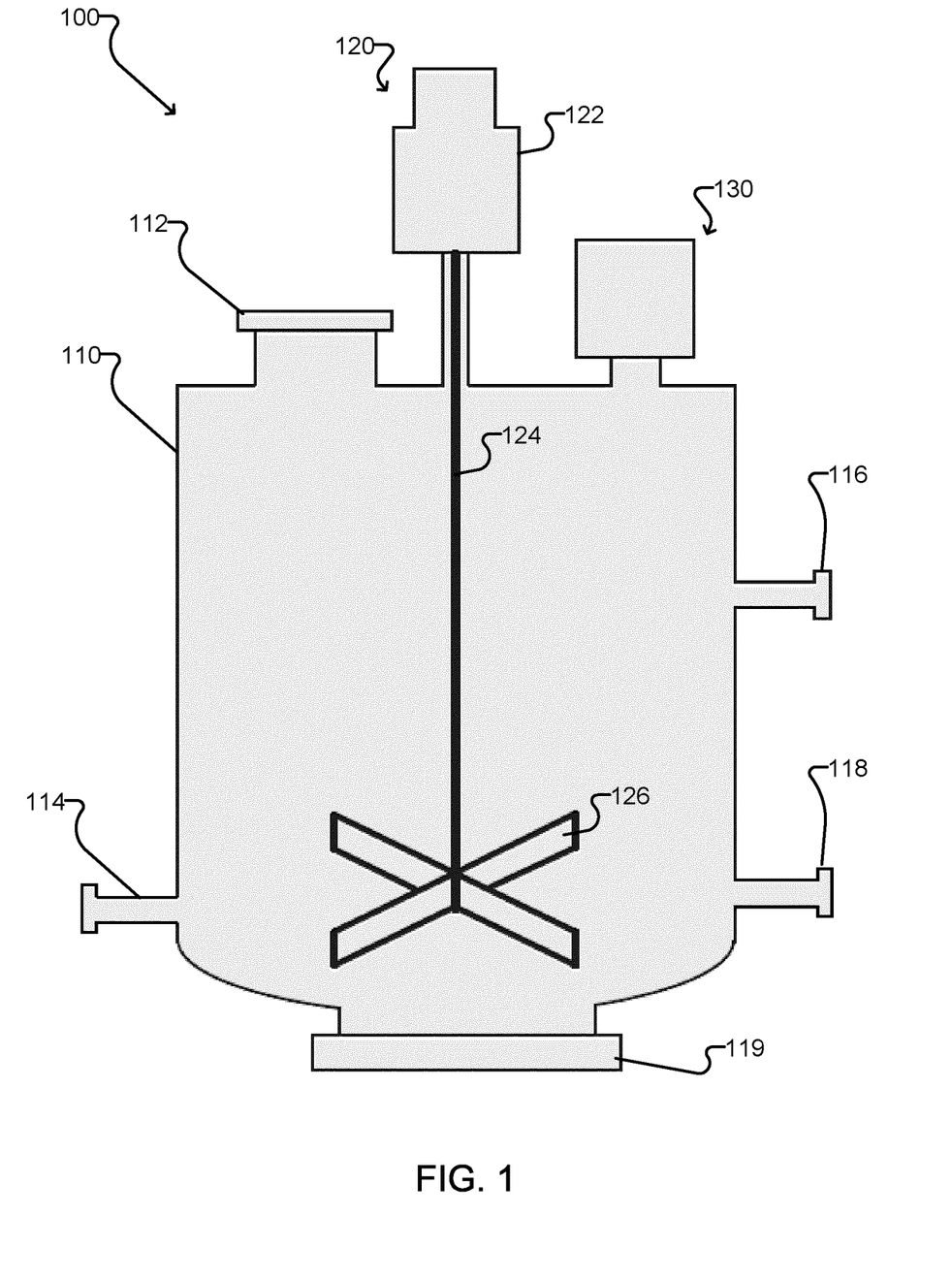
FIG. 1 shows an example container for carrying out a method of producing a terpene-rich extraction product according to one embodiment of the present disclosure.
Figure 2:
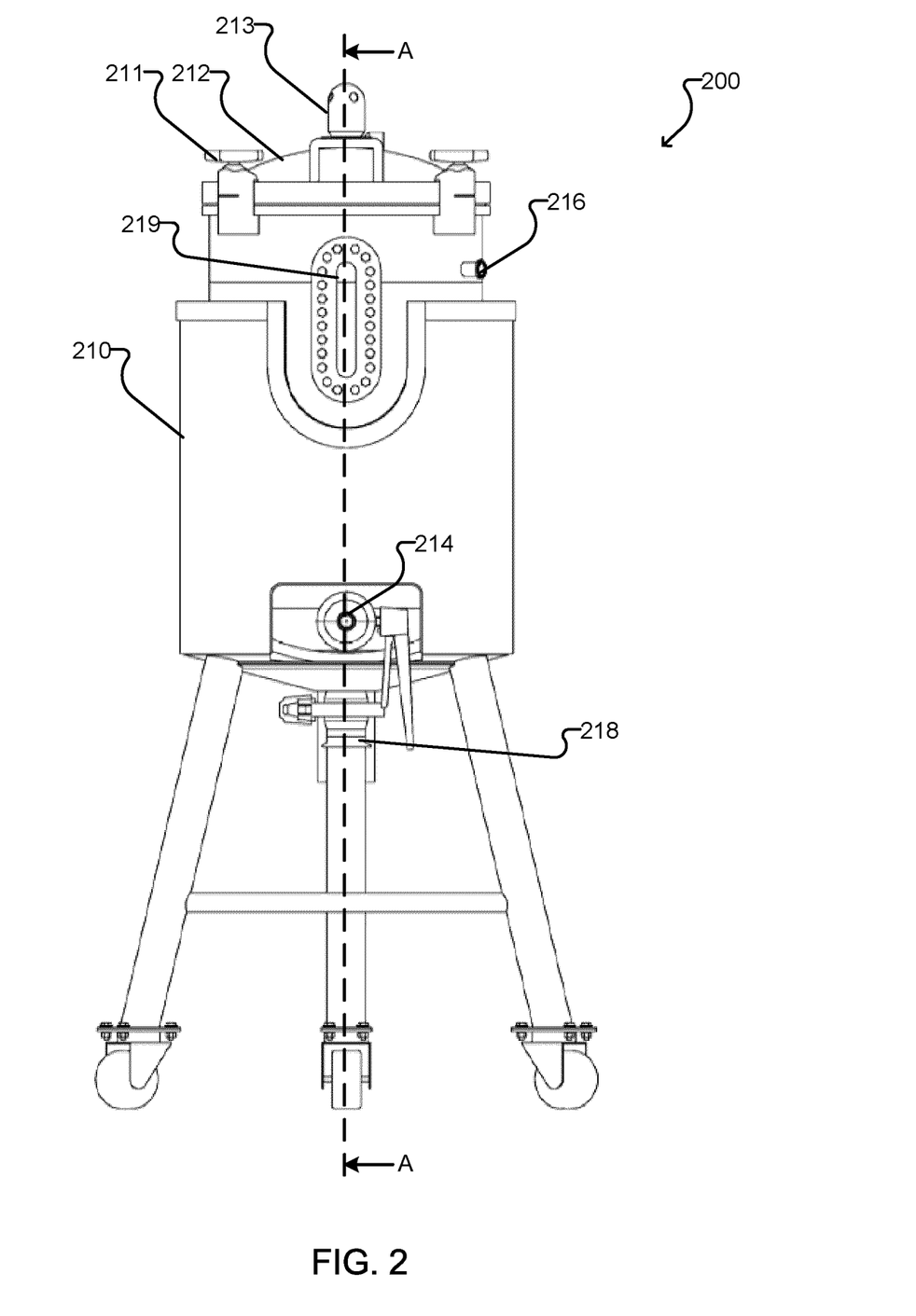
FIG. 2 shows another example container for carrying out a method of producing a terpene-rich extraction product according to one embodiment of the present disclosure.
Figure 2A:
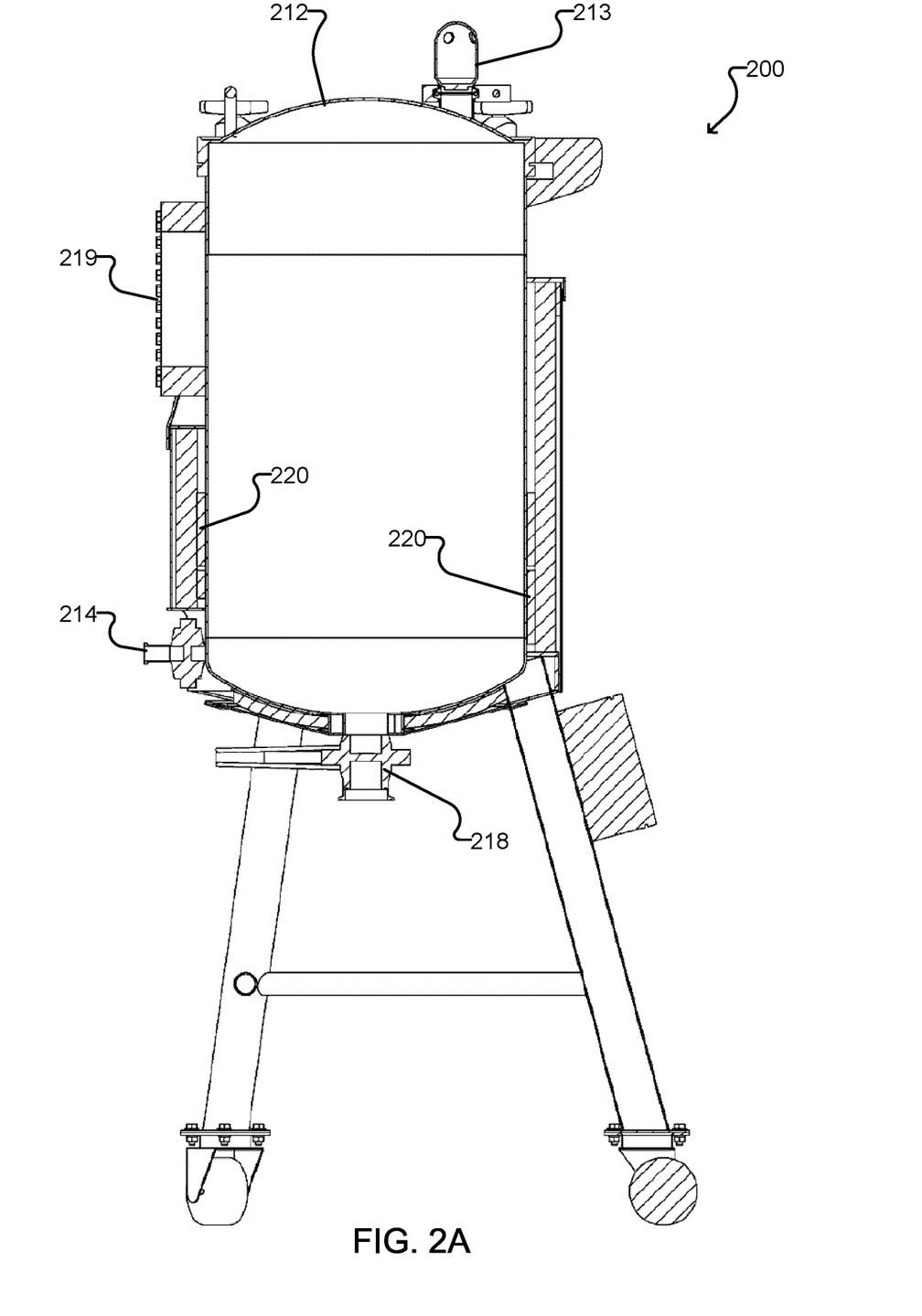
FIG. 2A is a sectional view taken along line A-A in FIG. 2.
Figure 2B:
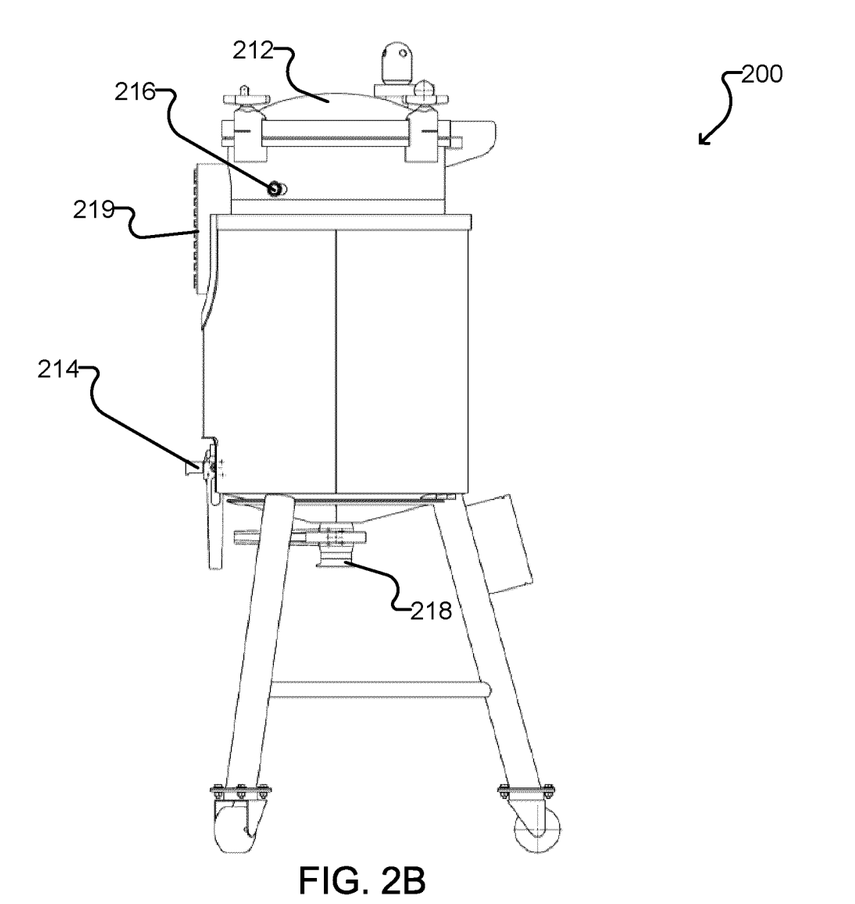
FIG. 2B is a side view of the container of FIG. 2.
Figure 2C:
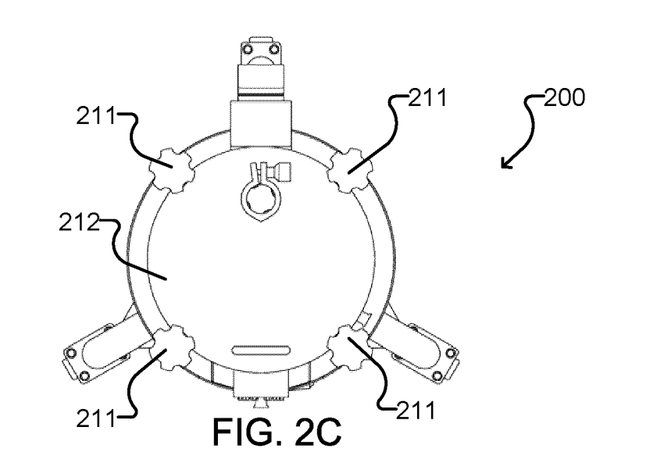
FIG. 2C is a top view of the container of FIG. 2.

The resin and extractor are placed into a sealed container. FIG. 1 shows an example container 100 for carrying out an extraction process according to the present disclosure. The container 100 comprises a sealed housing 110, having an agitator 120 and a pressure and temperature controller 130. The housing 110 has an input port 112 for receiving the resin/extractor mixture, a water inlet port 114 for receiving water, a product port 116 for removal of terpene enriched extracts, and an outlet port 118 for removal of water and remaining resin/extractor. A resin output hatch 119 may be provided at the bottom of the container 119 for removing settled resins from the housing 110, for example at the end of a batch process.

In the illustrated example, the agitator 120 comprises a motor 122, shaft 124 and impeller 126. The agitator 120 may take different forms in other embodiments.

The resin and extractor are mixed in the container 100 by the agitator 120 to create a resin/extractor mixture, which is heated to extract cannabis material (cannabinoids and terpenes). In some embodiments, the resin/extractor mixture is heated for about 20-60 minutes before filtering any resin or adding any water, as described below. In some embodiments, some or all of the depleted resin can optionally be filtered out of the mixture at this point in the process. For example, in situations where there is a lot of resin present, some of the resin may be filtered out before decarboxylation and may be further dissolved in the same extractor after decarboxylation. In some embodiments, depleted resin can optionally be filtered out after decarboxylation.

To decarboxylate, water is added to the mixture at a 1:1 ratio (by mass) with the oil or solvent. The mixture of cannabis resin/extractor/water (or extractor/water if resin is already filtered out) is cooked at a temperature in a range of approximately 90-140 Celsius under pressure in a range of approximately 0-420 kPa above atmospheric pressure for a time period of about 1-24 hours to decarboxylate the cannabinoids. In some embodiments, the mixture of cannabis resin/extractor/water is cooked at a temperature of approximately 125 Celsius under pressure in a range of approximately 0-150 kPa (or approximately 80 kPa in some examples) above atmospheric pressure for a time period of about 2-3 hours. After cooking, the mixture is typically left to cool for about 8-24 hours after the cooking period.

After the mixture has separated, the oil or solvent at the top of the container will form a high-quality extraction product, and is removed from the container 100, for example by decanting or siphoning through the product port 116. Water may be added to the bottom of the container 100 through the water inlet port 114 to raise a level of an interface between the top layer consisting of the high-quality extraction product and a lower layer with the water/resin to near the level of the product port 116. Any suitable process may be used for removing the extraction product from the upper portion of the container, so long as it does not include any, or at least no significant amount, of the resin or water at the bottom of the container. For example, in some embodiments the layer of high quality extraction product may be removed from the container 100 by a pipette or by using a beaker to decant the extraction product. The extraction product may also be passed through a filter in some embodiments.

If an edible oil was used, the extraction product removed from the product port 116 is the final product and will be the most terpene rich extract. If a solvent was used then the solvent is evaporated, and residues removed to create the final product, but this results in some terpene loss. These extraction products (whether obtained using either edible oil or solvent as the extractor) are considered the highest quality and should not have any residual water and are referred to herein as "primary extraction products".

The remaining residual mixture of extractor, resin and water left over after decanting is removed from the container 100, for example through the outlet port 118, then passed through a filter and the resin removed from the water and extractor. Water and extractor are separated in a funnel. The remaining oil or extract is considered second quality and contains residual water and is referred to herein as a "secondary extraction product".

The secondary extraction product can be dried with a drying agent, or heated with more water again and first quality siphoned off to turn it into higher quality product of similar quality to the primary extraction products. The secondary extraction product can also be added to the start of a new production cycle as part of the extractor input.

Resin that has been separated by filtration (either before or after decarboxylation) will often still contain up to 5% cannabinoids when dried (usually 1-3%) and can be used as a flour substitute for making cannabis edibles.

FIGS. 2, 2A, 2B and 2C show another example container 200 for carrying out an extraction process according to the present disclosure. The container 200 comprises a sealed housing 210, having a lid 212 with a pressure relief valve 213 thereon. The lid 212 can be opened to receive resin and extractor, and is held closed by closures 211. An agitator can be inserted into the interior of the housing 210 to mix the resin and extractor while the lid 212 is open. The housing has an input port 214 in a lower side portion thereof, a product output 216 in an upper side portion thereof, and an outlet port 218 and the bottom thereof. In some embodiments the outlet port 218 includes a built-in valve. In some embodiments the outlet port 218 includes a built-in filter.

The housing 210 also has a viewing window 219 along the side thereof. The viewing window 219 is positioned to provide a user with a view of the contents of the interior of the housing 210 from a height of the product output 216 to a predetermined height below the product output 216, such that the user can see the height of a top layer of high-quality extraction product on top of the separated mixture.

In some embodiments, the container 200 also has heating elements 220 built into the walls thereof. The walls of the container may be insulated in some embodiments.

In an example operation, resin and extractor are added through the open lid 212, and optionally mixed manually or by means of an agitator apparatus. In some embodiments, the resin and extractor may be heated while mixing to create a mostly homogeneous solution. The lid 212 is closed, water is added and the mixture is cooked to decarboxylate the cannabinoids. The mixture may be cooked, for example under high temperature and high pressure as described above. After the cook, pressure is relieved via a tee connected near 213, and then additional water is introduced through port 214 to raise the liquid level until the bottom of the top layer of high-quality extraction product gets near the product port 216 so that the oil exits through the product port 216. Once, the high-quality product has been removed, the remaining material is removed by opening the outlet port 218. The material may be removed by a combination of gravity and compressed air introduced through port 216. After the material has been removed, the lid 212 is opened up for access for cleaning the interior of the container 200.

Figure 3A:
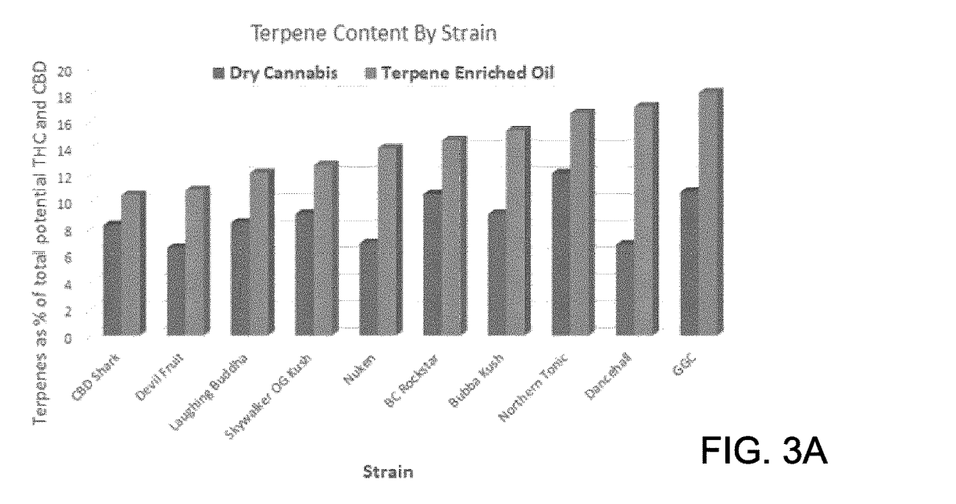
FIG. 3A shows terpene content of dry cannabis and extraction products made by example methods according to the present disclosure for different strains.
Figure 3B:
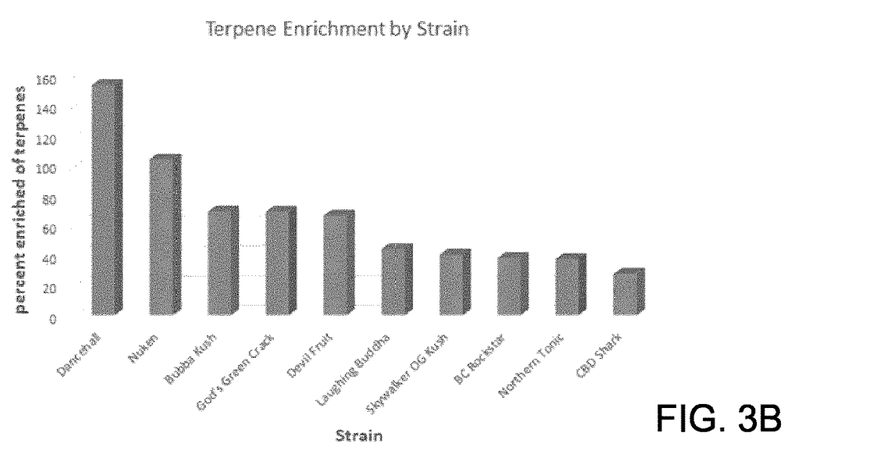
FIG. 3B shows the percentage of terpene increase from dry cannabis to extraction products made by example methods according to the present disclosure for different strains.
Figure 3C:
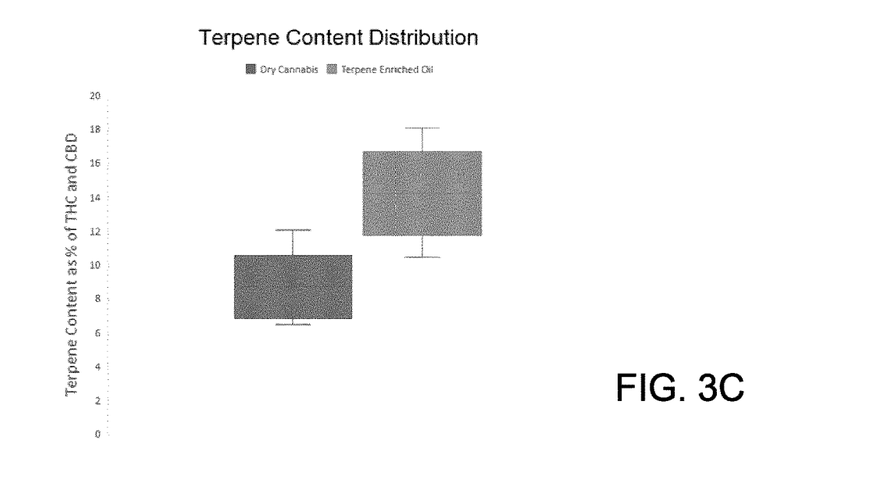
FIG. 3C shows the distribution of terpene contents for dry cannabis strains and extraction products made by example methods according to the present disclosure.

In some embodiments, the high quality extraction product has a cannabinoid to terpene ratio (by mass) in the range of 5:1 to 20:1, although this ratio may vary depending on the strain(s) of cannabis used for the starting material. For example, FIGS. 3A to 3C illustrate results of a comparison between a high-quality extraction product made using resin from fresh/frozen product of a variety of cultivars or strains using coconut oil as the extractor, and dried plant material of the same cultivar/strain. FIG. 3A shows terpene content of dry cannabis and extraction products made by example methods according to the present disclosure, and FIG. 3B shows the percentage of terpene increase from dry cannabis to extraction products made by example methods according to the present disclosure, for a variety of different strains of cannabis. Dry cannabis from different strains can have different cannabinoid to terpene ratios, and the cannabinoid to terpene ratio for extraction products made by example methods according to the present disclosure do not necessarily correspond to the cannabinoid to terpene ratio for dry cannabis. For example, the "Dancehall" strain has one of the lowest cannabinoid to terpene ratios of those tested for dry cannabis and one of the highest cannabinoid to terpene ratios for the extraction product (and has the highest percentage enrichment), whereas the "CBD Shark" strain has a slightly higher (in comparison to Dancehall) cannabinoid to terpene ratio for dry cannabis but a significantly lower cannabinoid to terpene for the extraction product (and has the lowest percentage enrichment). However, as illustrated in FIG. 3C, which shows the distribution of terpene contents for dry cannabis strains and extraction products made by example methods according to the present disclosure, the extraction products from all strains tested in the illustrated example have higher cannabinoid to terpene ratios than any of the dry cannabis.

In some embodiments, the high quality extraction product may have a cannabinoid to terpene ratio (by mass) of about 1:1 when starting with a strain with high terpene content and low cannabinoid content. Dry cannabis typically has a cannabinoid to terpene ratio of about 15:1, and extracts produced by prior art solvent based techniques often have cannabinoid to terpene ratios of about 75:1. The extraction products created by methods according to the present disclosure are thus significantly terpene enriched compared to certain prior art products.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various example embodiments described herein.

The description provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As will be apparent to those skilled in the art in light of the foregoing disclosure, many alterations and modifications are possible to the methods and systems described herein. While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as may reasonably be inferred by one skilled in the art. The scope of the claims should not be limited by the embodiments set forth in the examples, but should be given the broadest interpretation consistent with the foregoing disclosure.

The present disclosure may be embodied in other specific forms without departing from its spirit or essential characteristics. The described embodiments are to be considered in all respects only as illustrative and not restrictive.

The invention claimed is:
1. A method of producing cannabinoids and terpenes from cannabis resin, comprising:
   a) introducing a mixture of a cannabis resin; and an edible lipid or a hydrophobic organic solvent, into a sealed container;
   b) heating the mixture in the sealed container to extract cannabinoids and terpenes from the resin to produce an extracted cannabinoid/terpene mixture;
   c) adding water to the extracted cannabinoid/terpene mixture in the sealed container;
   d) decarboxylating the cannabinoids by heating the extracted cannabinoid/terpene mixture and water in the sealed container at a temperature in a range of approximately 90° C. to 140° C. under a pressure of up to approximately 420 kPa over atmospheric pressure for a period of about 1-25 hours to produce a decarboxylated cannabinoid/terpene mixture;
   e) allowing the decarboxylated cannabinoid/terpene mixture and water to cool and separate in the sealed container for a period of about 8-24 hours; and f) removing the decarboxylated cannabinoid/terpene mixture from the upper portion of the sealed container.

2. The method of claim 1, wherein decarboxylating the cannabinoids by heating the extracted cannabinoid/terpene mixture and water comprises heating at a temperature of approximately 125° C. and a pressure of up to 150 kPa over atmospheric pressure.

3. The method of claim 2, comprising heating at a pressure of approximately 80 kPa over atmospheric pressure for a period of 2-3 hours.

4. The method of claim 1, wherein the decarboxylated cannabinoid/terpene mixture comprises a terpene to cannabinoid ratio by mass in the range of about 1:20 to 1:1.

5. The method of claim 1, wherein terpenes comprise at least 5% of the active compounds in the decarboxylated cannabinoid/terpene mixture.

6. The method of claim 1, comprising filtering the cannabis resin from the extracted cannabinoid/terpene mixture after extracting cannabinoids and terpenes.

7. The method of claim 6, wherein filtering the cannabis resin occurs prior to heating the extracted cannabinoid/terpene mixture.

8. The method of claim 1, wherein introducing the mixture into the sealed container comprises introducing fresh cannabis resin and an edible lipid.

9. The method of claim 8, wherein introducing the mixture into the sealed container comprises introducing fresh cannabis resin and a hydrophobic organic solvent.

10. The method of claim 8, comprising evaporating solvent and removing residues from the decarboxylated cannabinoid/terpene mixture.

11. The method of claim 1, wherein adding water to the extracted cannabinoid/terpene mixture comprises adding water in a 1:1 ratio, by mass, with the edible lipid or a hydrophobic organic solvent.

12. The method of claim 1, comprising removing a residual mixture from the bottom portion of the sealed container and separating the water and the extractor from the residual mixture to produce a secondary extraction product.

13. The method of claim 12, comprising introducing the secondary extraction product into the sealed container with the mixture.

14. The method of claim 1, comprising obtaining the cannabis resin from the mixture by separating the cannabis resin from fresh cannabis.

15. The method of claim 14, wherein the cannabis resin is mixed with the extractor immediately after separating the cannabis resin from cannabis.

16. The method of claim 1, wherein the sealed container has an inlet port in a lower portion thereof and a product port in the upper portion thereof, and wherein removing the active extraction product from the upper portion of the sealed container comprises introducing additional water into the inlet port until a height of the bottom of the top layer of the active extraction product is near a height of the product port.

* * * * *